United States Patent
Gray et al.

(10) Patent No.: US 10,002,235 B2
(45) Date of Patent: Jun. 19, 2018

(54) MEDICAL DEVICE MANAGEMENT AND THEFT INHIBITOR TECHNIQUES

(71) Applicant: Ivenix, Inc., Amesbury, MA (US)

(72) Inventors: George W. Gray, North Andover, MA (US); William C. McQuaid, Melrose, MA (US)

(73) Assignee: Ivenix, Inc., Amesbury, MA (US)

( * ) Notice: Subject to any disclaimer, the term of this patent is extended or adjusted under 35 U.S.C. 154(b) by 0 days. days.

(21) Appl. No.: 14/794,256

(22) Filed: Jul. 8, 2015

(65) Prior Publication Data
US 2016/0045661 A1    Feb. 18, 2016

Related U.S. Application Data

(60) Provisional application No. 62/036,784, filed on Aug. 13, 2014.

(51) Int. Cl.
*G06F 7/04* (2006.01)
*G06F 15/16* (2006.01)
(Continued)

(52) U.S. Cl.
CPC .......... *G06F 19/3468* (2013.01); *A61B 90/90* (2016.02); *G06F 19/3418* (2013.01);
(Continued)

(58) Field of Classification Search
None
See application file for complete search history.

(56) References Cited

U.S. PATENT DOCUMENTS

| 6,189,105 B1 * | 2/2001 | Lopes | G06F 21/35 726/20 |
| 8,009,014 B2 * | 8/2011 | Eberhart | A61B 5/117 340/5.2 |

(Continued)

FOREIGN PATENT DOCUMENTS

| KR | 10-2009-0014446 | 2/2009 |
| KR | 10-2009-0030057 | 3/2009 |
| WO | 2013/099236 A1 | 7/2013 |

OTHER PUBLICATIONS

International Search Report, PCT/US2015/042615, dated Oct. 27, 2015, pp. 3.
(Continued)

*Primary Examiner* — Michael R Vaughan
*Assistant Examiner* — Vadim Savenkov
(74) *Attorney, Agent, or Firm* — Chapin IP Law, LLC

(57) ABSTRACT

A healthcare enterprise has an associated management resource that manages operation of one or more medical devices in the healthcare enterprise. To determine what functionality to enable in a respective medical device, the respective medical device establishes a communication link to communicate in a network environment. Subsequent to establishing the communication link, the medical device initiates communications over the communication link from the medical device to the remotely located management resource. The communications include a unique identifier value assigned to the medical device. Depending upon feedback (such as granting or denial of authorization) from the management resource with respect to the unique identifier value, the medical device operates in one of multiple different operational modes such as a fully functional mode or a reduced functionality mode.

27 Claims, 9 Drawing Sheets

(51) Int. Cl.
  *G06F 17/30* (2006.01)
  *H04L 29/06* (2006.01)
  *G06F 19/00* (2018.01)
  *A61B 90/90* (2016.01)
  *A61M 5/14* (2006.01)

(52) U.S. Cl.
  CPC ....... *A61M 5/14* (2013.01); *A61M 2205/3584* (2013.01); *A61M 2205/3592* (2013.01); *A61M 2205/52* (2013.01); *A61M 2205/6018* (2013.01)

(56) References Cited

U.S. PATENT DOCUMENTS

| | | | | |
|---|---|---|---|---|
| 2005/0283198 | A1* | 12/2005 | Haubrich | G06F 19/3418 607/30 |
| 2009/0002188 | A1* | 1/2009 | Greenberg | A01K 15/023 340/686.1 |
| 2009/0009283 | A1* | 1/2009 | Arts | G08B 13/1418 340/5.2 |
| 2011/0021140 | A1* | 1/2011 | Binier | H04B 5/0043 455/41.1 |
| 2011/0231204 | A1 | 9/2011 | De La Huerga | |
| 2011/0313922 | A1* | 12/2011 | Ben Ayed | G06Q 20/108 705/42 |
| 2012/0166680 | A1* | 6/2012 | Masoud | A61N 1/37235 710/8 |
| 2012/0226771 | A1* | 9/2012 | Harrington | G06F 19/3418 709/217 |
| 2013/0144206 | A1* | 6/2013 | Lee | A61M 5/1723 604/66 |
| 2014/0113553 | A1 | 4/2014 | Brukalo et al. | |
| 2014/0194817 | A1* | 7/2014 | Lee | A61M 5/14228 604/151 |
| 2014/0367256 | A1* | 12/2014 | Terashima | A61B 5/0022 204/403.01 |
| 2016/0029905 | A1* | 2/2016 | Kovacs | A61B 5/02055 600/301 |

OTHER PUBLICATIONS

Supplementary Search Report, EP 15 83 1836, dated Jul. 11, 2017, pp. 8.

* cited by examiner

MEDICAL DEVICE MANAGEMENT AND THEFT INHIBITOR TECHNIQUES

RELATED APPLICATIONS

This application claims the benefit of U.S. Provisional Patent Application Ser. No. 62/036,784 entitled "Medical Device Theft Inhibitor," filed on Aug. 13, 2014, the entire teachings of which are incorporated herein by this reference.

BACKGROUND

Conventional medical devices enable a caregiver in a hospital to provide medical care for patients. For example, one type of medical device is a fluid delivery pump. As is well known, a caregiver typically operates such a medical device to deliver a fluid-based drug to a patient. As with any medical device, the fluid delivery pump is susceptible to being removed (potentially without authorization) from a respective hospital environment and used elsewhere.

As medical devices such as fluid delivery pumps become more lightweight and mobile, they are increasingly susceptible to theft and improper removal. Conventional theft prevention technologies such as RFID tags, security cameras, etc., are expensive and difficult to administer, making it difficult to reduce theft or improper removal of medical devices. Tags of any sort, if used, are often very visible and easy to remove. Surveillance is easy to avoid because the medical device can be removed under cover by a person exiting a hospital environment.

BRIEF DESCRIPTION OF EMBODIMENTS

Embodiments herein include a novel approach to medical device theft prevention. In one embodiment, a medical device can be configured to operate only in a specific healthcare enterprise to which the medical device is assigned. When the medical device determines an attempt is being made to operate it in a foreign healthcare enterprise (i.e., a domain that is different than a domain to which the medical device is originally assigned), the medical device inhibits at least a portion of its available functionality, reducing its usefulness of providing care for patients within that enterprise.

As further discussed below, any suitable technique can be used to inhibit functionality in a respective medical device when it is unable to receive authorization from a management resource for use in an assigned domain (such as one or more contiguous or disparately located geographical regions). In one example embodiment, when a user operates a medical device within boundaries of a healthcare enterprise or domain to which it was a previously associated/assigned, the medical device operates in a potentially full functional mode. Conversely, when a user operates the medical device in a healthcare enterprise different from the previously associated/assigned healthcare enterprise, the medical device is denied authorization. In this latter instance, knowing it (i.e., the medical device) is being used improperly, the medical device prevents use of all or a portion of its functionality.

In accordance with further embodiments, the medical device can be configured to notify subsequent users of the device that it is operating in a foreign enterprise, indicating that the medical device may have been stolen or inadvertently removed from an originally assigned enterprise.

In accordance with more specific example embodiments, a healthcare enterprise (such as hospital) includes a management resource. The management resource manages operation of one or more medical devices in the healthcare enterprise. To determine what functionality to enable in a respective medical device, a respective medical device first establishes a communication link to communicate in a network environment. Subsequent to establishing the communication link, the medical device initiates communications over the communication link from the medical device to the remotely located management resource. Depending upon feedback from the management resource, the medical device operates in one of multiple different operational modes such as a fully functional mode or a reduced functionality mode. Such an embodiment deters theft of a respective medical device because the medical device supports a substantially reduced set of functionality when the medical device determines that an attempt is being made to operate the respective medical device in a domain that is different from the respective originally assigned domain (such as a healthcare enterprise that owns the medical device).

In accordance with yet more specific example embodiments, to support authorization, each of the medical devices managed by the management resource is assigned a key value unique to the corresponding enterprise domain to which the medical device is assigned/associated. Each of the medical devices assigned for use in a given enterprise stores a copy of the respective unique key value assigned to the assigned enterprise. In one embodiment, to determine what functionality to enable in a respective medical device, the medical device forwards the unique key value assigned to the medical device over the communication link to the management resource. The management resource then performs an analysis to determine whether the unique key value received from the medical device matches its own key (i.e., the unique key assigned to the corresponding enterprise domain).

If the management resource verifies that the unique key received from the medical device matches its own key (such as the key assigned to the enterprise), the management resource notifies the respective medical device that it is authorized to enable the functionality supported by the respective medical device.

Note that in a similar manner, the management resource can be configured to authorize any of multiple medical devices that provide an appropriate assigned unique key value. That is, each of the multiple medical devices acquired for use in the healthcare domain is assigned the unique key associated with the medical enterprise in which the devices will be used. In a manner as previously discussed, upon use, each of the multiple medical devices forwards the unique key to the management resource for verification as previously discussed.

Assume that a respective medical device is removed from the healthcare enterprise. Further assume that the management resource resides in a private network that is only accessible to the medical device if the medical device is located within a wireless communication range of the healthcare enterprise. In such an instance, the medical device is unable to communicate with the management resource disposed in the healthcare enterprise because the medical device resides outside of the private network. Because the medical device is unable to receive authorization from the management resource, the medical device continues to operate in the mode it operated when it last communicated with a healthcare enterprise. In other words, if the medical device had previously operated with reduced functionality such as due to denial of authorization, it would continue to do so until it reconnects to its associated healthcare enterprise. Conversely, if it was previously operating with full functionality such as because the medical device received authorization, it would continue to do so even though it is unable to communicate with the management resource to obtain authorization.

In accordance with yet further embodiments, note that whether or not a respective medical device operates in a full or reduced functionality mode as discussed above depends upon a setting assigned to the respective medical device. For example, in one embodiment, the medical device can be assigned configuration setting information indicating to the medical device that the medical device is "locked" to a particular healthcare enterprise domain. The configuration setting information can be stored in any suitable location such as in the medical device or at a remote location with respect to the medical device. In response to detecting a condition such as that the medical device is "locked" to a particular healthcare enterprise, the medical device communicates its assigned key to the management resource as discussed above to determine whether to operate in a fully functional mode or a reduced function mode.

Thus, in a manner as previously discussed, the user of a locked medical device can use full functionality of the medical device during conditions in which the management resource authorizes the functions in the medical device. Conversely, during conditions such as when the locked medical device attempts to pass an invalid key to a management resource, the locked medical device operates in a reduced functionality mode. This unique operation deters theft of the medical device because it has less value in a foreign healthcare provider domain when it is set to the locked mode. That is, in a remote domain other than the healthcare provider domain to which the medical device was associated, the locked medical device is prevented from executing one or more operations when denied authorization.

In accordance with still further embodiments, if desired and as further discussed herein, the configuration setting information assigned to the medical device can be set to an "unlocked" mode as opposed to being "locked." In this latter instance, the medical device can be operated in a similar manner (such as all functionality enabled) regardless of the healthcare enterprise in which it is operating.

These and other more specific embodiments are disclosed in more detail below. Note that any of the resources as discussed herein can include one or more computerized devices, medical devices, servers, base stations, wireless communication equipment, communication management systems, workstations, handheld or laptop computers, or the like to carry out and/or support any or all of the method operations disclosed herein. In other words, one or more computerized devices or processors can be programmed and/or configured to operate as explained herein to carry out different embodiments of the invention.

Yet other embodiments herein include software programs to perform the steps and operations summarized above and disclosed in detail below. One such embodiment comprises a computer program product including a non-transitory computer-readable storage medium (i.e., any physical computer readable hardware storage medium) on which software instructions are encoded for subsequent execution. The instructions, when executed in a computerized device (e.g., computer processing hardware) having a processor, program and/or cause the processor to perform the operations disclosed herein. Such arrangements are typically provided as software, code, instructions, and/or other data (e.g., data structures) arranged or encoded on a non-transitory computer readable storage medium such as an optical medium (e.g., CD-ROM), floppy disk, hard disk, memory stick, etc., or other a medium such as firmware or shortcode in one or more ROM, RAM, PROM, etc., or as an Application Specific Integrated Circuit (ASIC), etc. The software or firmware or other such configurations can be installed onto a computerized device to cause the computerized device to perform the techniques explained herein.

Accordingly, embodiments herein are directed to a method, system, computer program product, etc., that supports operations as discussed herein.

One embodiment herein includes a computer readable storage medium and/or system having instructions stored thereon. The instructions, when executed by computer processor hardware, cause the computer processor hardware to: initiate communications over a communication link from a medical device to a remotely located management resource; and selectively operate the medical device in one of multiple different operational modes depending on whether the medical device receives current or previous authorization of use from the management resource.

Another embodiment herein includes a computer readable storage medium and/or system having instructions stored thereon. The instructions, when executed by computer processor hardware, cause the computer processor hardware to: from a medical device, establish a communication link; via communications over the communication link, initiate registration of the medical device with a management server that controls an operational mode of the medical device; in response to detecting denial of authorization of the medical device, prevent activation of at least a portion of functionality in the medical device The ordering of the operations above has been added for clarity sake. Note that any of the processing steps as discussed herein can be performed in any suitable order.

Other embodiments of the present disclosure include software programs and/or respective hardware to perform any of the method embodiment steps and operations summarized above and disclosed in detail below.

It is to be understood that the system, method, apparatus, instructions on computer readable storage media, etc., as discussed herein also can be embodied strictly as a software program, firmware, as a hybrid of software, hardware and/or firmware, or as hardware alone such as within a processor, or within an operating system or within a software application.

As discussed herein, techniques herein are well suited for managing and facilitating use of medical devices in different environments. However, it should be noted that embodiments herein are not limited to use in such applications and that the techniques discussed herein are well suited for other applications as well.

Additionally, note that although each of the different features, techniques, configurations, etc., herein may be discussed in different places of this disclosure, it is intended, where suitable, that each of the concepts can optionally be executed independently of each other or in combination with each other. Accordingly, the one or more present inventions as described herein can be embodied and viewed in many different ways.

Also, note that this preliminary discussion of embodiments herein purposefully does not specify every embodiment and/or incrementally novel aspect of the present disclosure or claimed invention(s). Instead, this brief description only presents general embodiments and corresponding points of novelty over conventional techniques.

For additional details and/or possible perspectives (permutations) of the invention(s), the reader is directed to the Detailed Description section and corresponding figures of the present disclosure as further discussed below.

Figure 1:
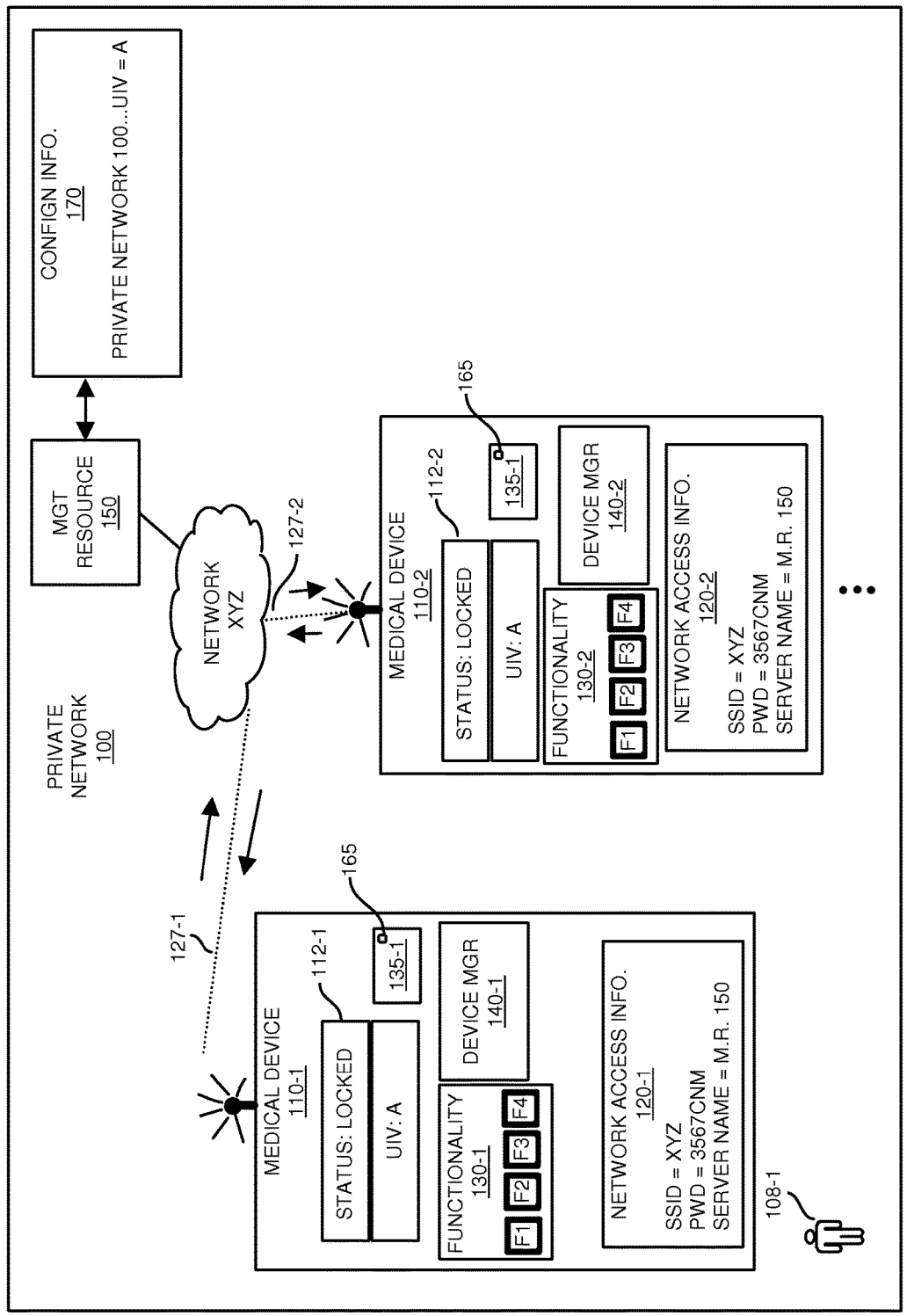
FIG. 1 is an example diagram illustrating implementation of a lock feature to control use of a medical device in a private network according to embodiments herein.

The foregoing and other objects, features, and advantages of the invention will be apparent from the following more particular description of preferred embodiments herein, as illustrated in the accompanying drawings in which like reference characters refer to the same parts throughout the different views. The drawings are not necessarily to scale, with emphasis instead being placed upon illustrating the embodiments, principles, concepts, etc.

DETAILED DESCRIPTION AND FURTHER SUMMARY OF EMBODIMENTS

Now, more specifically, FIG. 1 is an example diagram illustrating implementation of a lock feature to control/limit use of functionality in a medical device according to embodiments herein.

As shown in this example embodiment, the medical environment includes private network 100 in which medical device 110-1, medical device 110-2, etc., reside and are configured to operate.

Note that the medical devices 110 as described herein can be any type of medical device. For example, in one embodiment, the each of the medical devices 110 is an infusion pump use for delivery of fluid to a respective recipient. Each infusion pump can be configured to support different types of functionality such as first functionality supporting pumping of fluid from the medical infusion pump to a recipient, second functionality supporting retrieval of drug information over a network connection from a remote server resource disparately located with respect to the medical infusion pump, etc.

In this example embodiment, the configuration information 112 assigned to each of the medical devices 110 is set to a LOCKED operational mode, indicating that the respective medical devices 110 must satisfy one or more preconditions (such as registration, verification, authentication, authorization, etc.) or have no connection to a management resource within a healthcare enterprise before certain functionality is enabled for use by an operator of the respective medical device.

In accordance with an example embodiment, to determine what functionality to enable in a respective medical device, the respective medical device establishes a communication link to communicate with management resource 150.

More specifically, assume that user 108-1 attempts to operate or execute a function associated with medical device 110-1. In response to detecting receipt of a respective command and/or activation of the medical device 110-1, the device manager 140-1 must first determine what portion, if any, of the functionality 130-1 (such as functionality F2, functionality F2, functionality F3, functionality F4, etc.) to enable in the medical device 110-1 for use by the user 108-1.

More specifically, upon activation or receipt of a respective command with respect to the medical device 110-1 to perform a respective function, as previously discussed, the device manager 140-1 first determines whether it can connect with a management resource. If it cannot communicate with a respective management resource, the medical device operates in the mode it last operated when it connected to a management resource. That is, if the medical device 110-1 was previously authorized for use, then the medical device 110-1 supports full functionality. If the medical device 110-1 was previously denied authorization, then the medical device 110-1 supports limited functionality until receiving further authorization.

In this example embodiment, the medical device 110-1 determines whether or not the medical device is being implemented in a LOCKED or UNLOCKED mode as mentioned above. To determine a respective mode setting, the device manager 140-1 accesses device configuration setting information 112-1 indicating that the medical device 110-1 is set to a LOCKED mode.

Note that the device configuration setting information 112-1 can be stored locally or, alternatively, at a remote location with respect to medical device 110-1.

Further in this example embodiment, in response to detecting that the device setting information 112-1 indicates that the medical device 110-1 is set to the LOCKED mode, the device manager 140-1 is therefore informed that use of certain functionality 130-1 such as use of functions F3 and function F4 supported by the respective medical device 110-1 are conditional. Functions F1 and F2 may be used by the respective user 108-1 without conditions. In other words, the device manager 140-1 of the medical device 110-1 can be configured to enable functions F1 and F2 as a default condition regardless of whether or not the device manager 140-1 is LOCKED or UNLOCKED and receives authorization from the management resource 150.

To enable a portion of functionality such as functions F3 and F4 that require authorization because the device 110-1 is LOCKED, the device manager 140-1 must either be running disconnected from any management resource or register with and/or be authorized by the controller such as management resource 150 to use such functionality.

In one embodiment, functionality F1 supports pumping of fluid from the medical device 110-1 (such as an infusion pump) to a recipient, functionality F3 supports retrieval of drug information over a network connection from a remote server resource disparately located with respect to the medical device, etc.

To register/verify authorization of the medical device 110-1 for use of locked functionality F3 and F4, the device manager 140-1 utilizes the network access information 120-1 to identify an appropriate authority to contact. In this example embodiment, the network access information 120-1 indicates the name of a wireless network (such as network XYZ including one or more wireless or WiFi™ access points) to which the medical device 110-1 must connect in order to communicate with management resource 150 (control authority) . Note that network XYZ can be or include a packet-switched network, the Internet, WiFi™ network, etc., facilitating communications between medical devices 110 and a respective manager resource 150. Further note that the manager resource 150 can be a logical entity including multiple disparately located servers.

Assume in this example embodiment that the medical device 110-1 is able to establish a respective communication link 127-1 with a wireless access point in network XYZ using the SSID=network name network XYZ and corresponding password/passkey 3567CNM as specified by network access information 120-1. In one embodiment, the wireless access point in network XYZ requires the medical device 110-1 to use the password/passkey 3567CNM to establish wireless communication link 127-1 as a secured communication link in network XYZ.

Subsequent to establishing the respective communication link 127-1 (such as a secured link), the device manager 140-1 initiates communications with a target recipient such as the management resource 150 as specified by the network access information 120-1. In one embodiment, the server name in network access information 120-1 is a text-based link or string of data specifying a unique name (such as Healthcare Clinic XYZ) of the private network 100 in which the medical device 110-1 is configured for use. In such an instance, to access the management resource 150, the device manager 140-1 of the medical device 110-1 uses the server name (such as Healthcare Clinic XYZ) to obtain a corresponding network address assigned to the management resource 150. Via subsequent communications addressed to the management resource 150 using the corresponding network address, the device manager 140-1 communicates with the management resource 150 over network XYZ.

In the embodiment as shown, the private network 100 is assigned a corresponding unique identifier value (such as unique key value A). To support authorization, each of the medical devices managed by the management resource 150 is also assigned the unique identifier value (i.e., unique key value A). The manager resource 150 has knowledge of and keeps track of the unique identifier value A assigned to the private network 100 as shown in configuration information 170.

Any suitable technique can be used to provide notification to the management resource 150 that a respective medical device has been assigned a corresponding unique identifier value and should be authorized for use of full functionality.

For example, in one embodiment, as previously discussed, the management resource 150 managing operation of the medical devices 110 stores a copy of the respective unique identifier value A assigned to the private network 100.

In one embodiment, the private network 100 (located within an enterprise, domain, etc.) can be a single network within a defined perimeter that provides wireless connectivity to medical devices 110 residing within a corresponding geographic region in the defined perimeter.

Alternatively, note that the private network 100 of a particular healthcare provider can include multiple disparately located sub-networks, each of which is assigned the same respective unique identifier value A. For example, private network 100 (operated by a particular healthcare provider) can include a first sub-network (such as in a first office location) and a second sub-network (such as in a second office location) that each provide wireless coverage in a disparately located geographical regions. As an illustrative example, the first sub-network can be configured to operate in a first geographical region in a first city, the second sub-network can be configured to operate in a second geographical region in a second city.

Each of the sub-networks can be configured to support wireless connectivity to management resource 150 because such sub-networks are part of the same logical private network 100. In such an instance, both of the sub-networks and corresponding medical devices associated with the corresponding service provide and operated therein are assigned the unique identifier value A. The medical devices assigned the unique identifier value A can be used in any of the sub-networks. For example, when a corresponding medical device 110-1 resides within the first geographical region supported by the first sub-network, the medical device 110-1 communicates with the management resource 150 through the first sub-network of private network 100. When the corresponding medical device 110-1 resides within the second geographical region supported by the second sub-network, the medical device 110-1 communicates with the management resource 150 through the second sub-network of private network 100. When the medical device 110-1 is operated outside of the first geographical region and a second geographical region, the medical device 110-1 is unable to communicate with the management resource 150.

Accordingly, the domain, enterprise, etc., as discussed herein can be a single contiguous geographical region or multiple disparately located geographical regions that are assigned the unique identifier value A.

To determine what functionality to enable in a respective medical device, during the communications as discussed above, a respective medical device 110-1 retrieves respective unique identifier value A (such as a key) from configuration information 112-1 assigned to medical device 110-1. The respective unique identifier value A can be stored in any suitable location that is not accessible to users.

In general, the device manager 140-1 uses the unique identifier value A assigned to the medical device 110-1 to register the medical device 110-1 with the management resource 150. For example, in a more specific embodiment, the device manager 140-1 communicates a respective registration/verification request to the management resource 150 over communication link 127-1 and network XYZ to manager resource 150. The management resource 150 responds with an appropriate URI in which to forward the unique identifier value A assigned to the medical device 110-1 over the network XYZ to a target recipient. The device manager 140-1 then forwards the unique identifier value A (key information) to the address as specified by the URI.

The management resource 150 then performs an analysis of the received unique identifier value A to determine whether the unique identifier value A received from the medical device 110-1 matches the stored copy of the unique identifier value for private network 100.

If the management resource 150 verifies that the unique identifier value A received from the medical device 110-1 matches the unique identifier value stored in configuration information 170 indicating that the medical device 110-1 is assigned for use in the private network 100, the management resource 150 notifies the respective medical device 110-1 that it is authorized to enable functionality (such as conditional LOCKED functionally F3 and F4) associated with the respective medical device 110-1.

More specifically, in this example embodiment, the management resource 150 compares the received unique identifier value A from medical device 110-1 to a copy of the unique identifier value A assigned to the private network 100 and stored in configuration information 170. Since the received unique identifier value from medical device 110-1 matches the unique identifier value A in the configuration information 170, the management resource 150, via communications in a reverse direction over the wireless communication link 127-1 and network XYZ, provides notification to the device manager 140-1 in medical device 110-1 that the medical device 110-1 and corresponding functionality 130-1 is authorized/verified for use in private network 100.

In a similar manner, the management resource 150 can be configured to authorize any of multiple medical devices that provide an appropriate assigned unique key value. For example, upon activation of medical device 110-2 for input of a respective command to execute functionality 130-2, the device manager 140-2 utilizes the network access information 120-2 to establish respective communication link 127-2 with network XYZ in a similar manner as previously discussed. Further in this example, the device manager 140-2 utilizes the unique identifier value A assigned to the medical device 110-2 to register the medical device 110-2 with management resource 150. Upon verification of the medical device 110-2 based on the unique identifier value A forwarded from the medical device 110-2 to the management resource 150, the management resource 150 verifies the medical device 110-2 and notifies the device manager 140-2 of the medical device 110-2 to enable an appropriate LOCKED portion of functionality 130-2 (such as functionality F3 and F4) associated with the medical device 110-2.

In accordance with further embodiments, assume that the user 108-1 removes (such as due to theft, inadvertent error, etc.) the medical device 110-1 from the private network 100 such that the medical device 110-1 is now out of wireless communication range with respect to network XYZ. In such an instance, the medical device 110-1 is no longer able to communicate over communication link 127-1 and network XYZ to the management resource 150.

Even though the medical device 110-1 is now out of range with respect to the private network 100 the device manager 140-1 can be figured to continue enabling use of any or all of functionality 130-1 that does not rely on communication with the management resource 150.

Note that subsequent to authorization of respective functionality 130-1 as described herein, and on an as-needed basis, the device manager 140-1 of the medical device 110-1 can be configured to additionally utilize the server name assigned to management resource 150 or other server name to communicate over the communication link 127-1 to support functionality F3 and F4.

Figure 2:
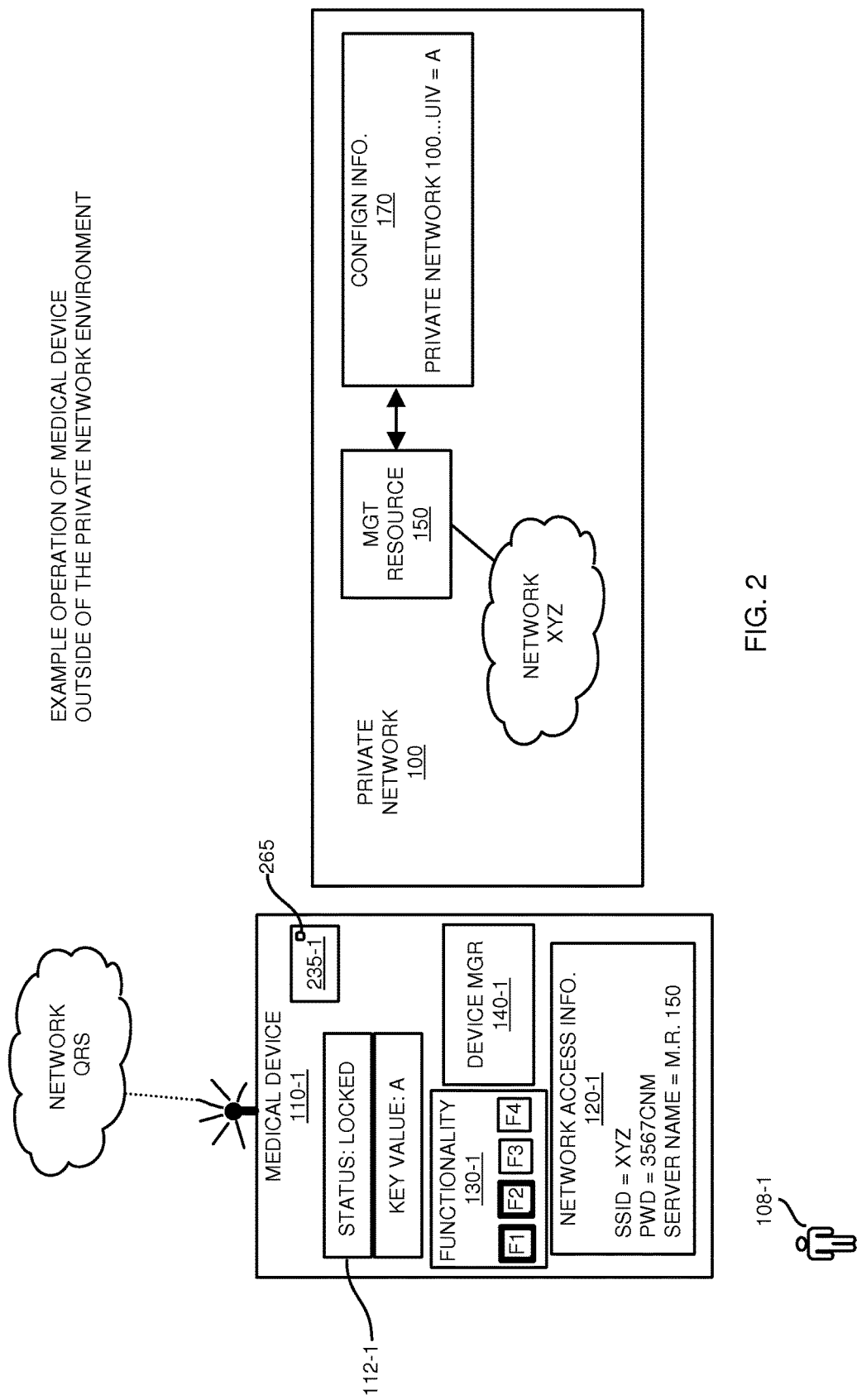
FIG. 2 is an example diagram illustrating implementation of a lock feature to control use of a medical device located outside a private network according to embodiments herein.

FIG. 2 is an example diagram illustrating implementation of a lock feature to control use of a medical device located outside a private network according to embodiments herein.

Upon detecting next use (such as next power-up or after some timeout value) of the medical device 110-1, as shown in FIG. 2, the medical device 110-1 attempts to communicate with the management resource 150 to receive authorization to enable functionality LOCKED F3 and F4 in the medical device 110-1. In this instance, device manager 140-1 again accesses the configuration information 112-1 to learn that it is LOCKED for use in a private network.

Upon detecting a condition such as that the user 108-1 powers up the medical device 110-1 or attempts to use a function associated with the medical device 110-1 while in a foreign network, the device manager 140-1 utilizes the network access information 120-1 to attempt registration/authorization with the management resource 150 for use of one or more functions. However, in this instance, because the medical device 110-1 is operated in a foreign network (as opposed to being operated in private network 100), the medical device 110-1 is denied authorization to enable functionality F3 and F4.

In this example embodiment, because the device manager 140-1 is denied authorization, the device manager 140-1 enables only default functionality F1 and F2 in the medical device 110-1. The device manager 140-1 prevents use of functionality F3 and F4.

Thus, setting the status of the configuration 112-1 in the medical device 110-1 to a LOCKED mode inhibits use of functionality F3 and F4 in a foreign network or at any time subsequent to establishing a connection to that network until the medical device 110-1 is returned to its associated and LOCKED network (private network 100).

Thus, whether or not a respective device manager in a medical device operates in a full or reduced functionality mode depends upon a configuration setting information assigned to the respective medical device. That is, as discussed herein, the user of a LOCKED medical device can use full functionality of the medical device during conditions in which a management resource authorizes or has previously authorized the functions in the medical device.

As described herein, authorization of a respective medical device may be contingent upon the location of the respective medical device. For example, the LOCKED medical device 110-1 can communicate and register with the management resource 150 only when the medical device 110-1 is within wireless communication range of network XYZ.

Additionally, during conditions such as when the medical device is unable to communicate with the management resource to obtain authorization, such as because the medical device 110-1 is out of communication range with respect to the network XYZ or simply because there is some type of connection failure, the corresponding device manager 140-1 continues to provide the same level of functionality provided the last time it was granted or denied that authorization. This deters theft of the medical device because it has less value when operating in a healthcare provider domain other than the one in which it is associated and LOCKED.

In accordance with further embodiments, in response to detecting a condition in which the medical device 110-1 is unable to receive authorization from the management resource via communications over a respective communication link as specified by corresponding network access information, the device manager 140-1 provides notification 265 on display screen 235-1 to an operator (such as user 108-1) of the medical device 110-1.

The notification 265 can indicate any suitable type of information such as: i) a medical service provider XYZ to which the medical device belongs or is registered or LOCKED to, ii) that the medical device 110-1 is restricted to operating in a limited operational mode because the medical device 110-1 is LOCKED and has detected that a user attempted to operate it in a foreign network 100 (result in denial of authorization), iii) that the medical device 110-1 is stolen, iv) which functionality of the medical device 110-1 is disabled based on its last registration attempt with a management resource, v) which functionality of the medical device 110-1 is enabled for use, etc.

Further embodiments herein can include producing the notification 265 to indicate that the medical device 110-1 is configured in a respective LOCKED mode or UNLOCKED MODE depending upon configuration settings 112-1.

Figure 3:
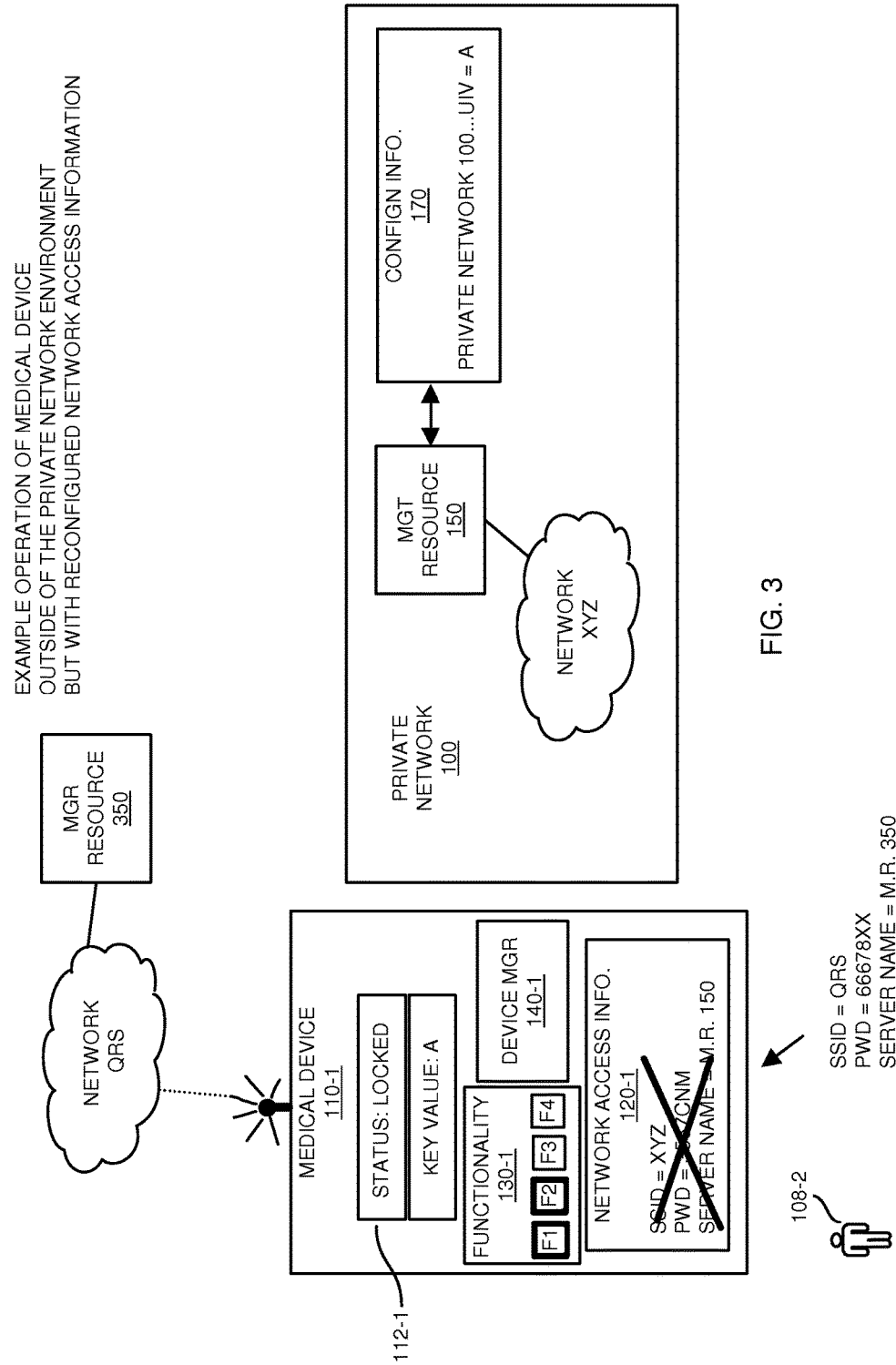
FIG. 3 is an example diagram illustrating implementation of a lock feature to control use of a medical device located outside of a private network according to embodiments herein.

FIG. 3 is another example diagram illustrating implementation of a lock feature to control use of a medical device located outside of an assigned private network according to embodiments herein.

As shown in FIG. 3, a respective user such as user 108-2 can reprogram the network access information 120-1 such that the device manager 140-1 is directed to a different selected server when attempting to verify use of a respective functionality 130-1.

In this example embodiment, assume that the user 108-2 now possesses medical device 110-1 (potentially after being stolen) and reprograms network access information 120-1 to indicate an SSID of QRS, a password of 66678XX, and a server name specifying management resource 350. Thus, the user 108-2 programs the network access information 120-1 to use the medical device 110-1 at a new location through a new network QRS.

In this instance, when the user 108-2 attempts to use functionality (such as by turning the device to an ON state, by attempting to use any of functionality 130-1, by providing input to connect to manager resource 350, by inputting a respective command, operating a graphical user interface, etc.) associated with medical device 110-1, the device manager 140-1 checks the configuration information 112-1 to learn that it is a respective LOCKED device.

Based the on this new configuration setting information 112-1, the device manager 140-1 attempts to communicate with a management resource as specified by the new network access information 120-1. The device manager 140-1 uses the SSID value (QRS) to connect with network QRS using password 66678XX.

Via the established communication link with network QRS, the device manager 140-1 attempts to register and/or obtain authorization of the medical device 110-1 for use with management resource 350. However, the management resource 350 is unable to authorize and/or authenticate the medical device 110-1 because the management resource 350 does not possess the same corresponding unique identifier value A assigned to the medical device 110-1. In other words, the management resource 350 is unable to authorize medical device 110-1 for use, the management resource 350 denies authorization. Thus, even though the user 108-2 attempts to use the medical device outside of private network 100, the device manager 140-1 prevents operation of LOCKED functionality F3 and F4.

However, as previously discussed, the medical device 110-1 can be configured to allow use of UNLOCKED default functionality F1 and F2.

Figure 4:
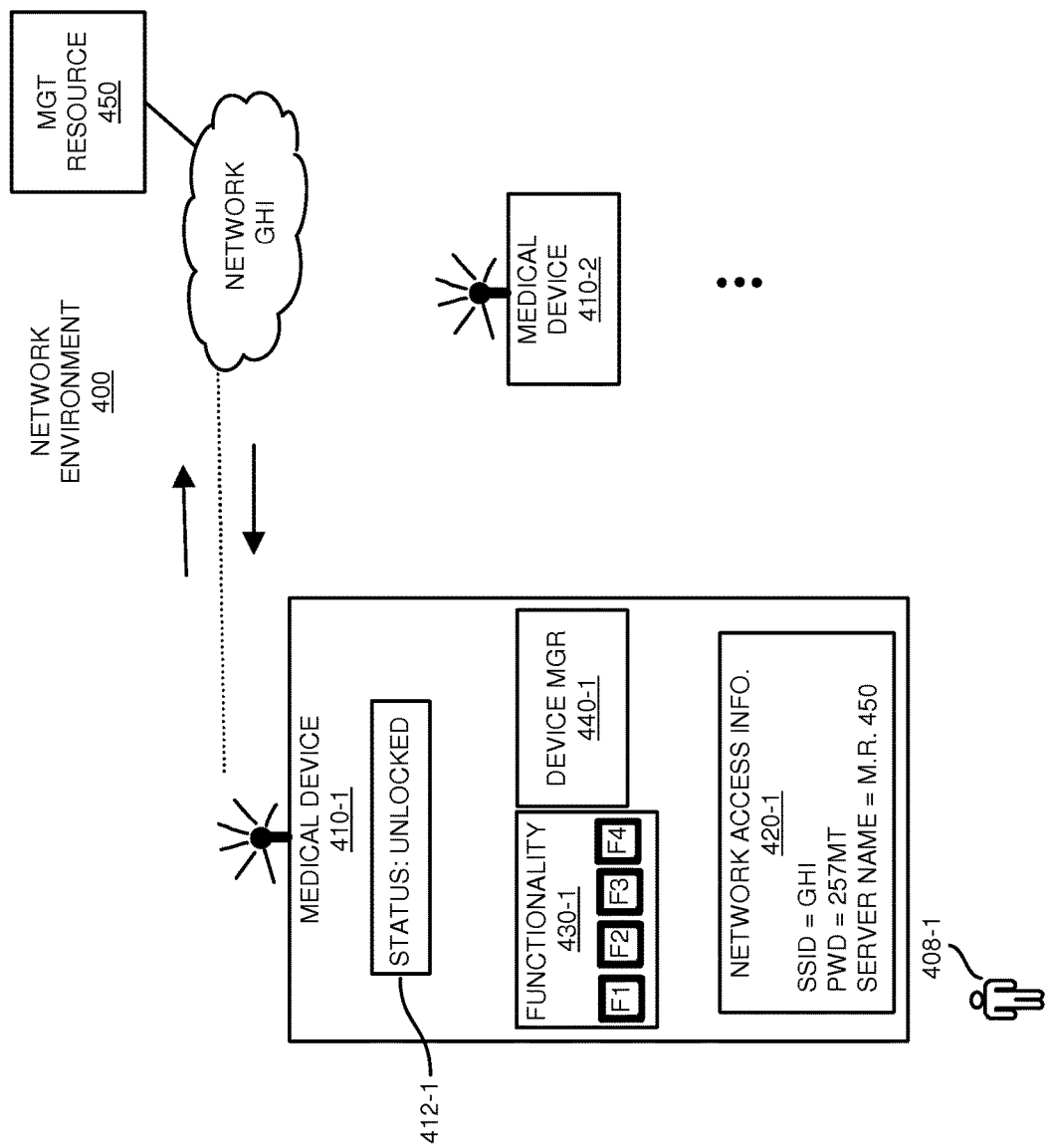
FIG. 4 is an example diagram illustrating implementation of a medical device in an unlocked operational mode according to embodiments herein.

FIG. 4 is an example diagram illustrating implementation of a medical device in an unlocked operational mode according to embodiments herein.

In this example embodiment, assume that a medical service provider operating in network environment 400 controls use of medical devices 410 (such as including medical device 410-1, medical device 410-2, etc.). However, instead of configuring each of the medical devices 410 to be in a LOCKED mode as previously discussed, assume that service provider GHI (to which the medical devices 410 belong) sets configuration settings 412-1 to indicate that each of the medical devices is set to an UNLOCKED mode. The UNLOCKED mode indicates that functionality associated with the respective medical device 410-1 can be used in any suitable environment.

For example, in response to detecting activation of the medical device 410-1 by the user 408-1, the device manager 440-1 checks configuration information 412-1 to determine whether or not the medical device 410-1 is locked or unlocked. In this example, in response to detecting that the medical device 410-1 is set to an UNLOCKED mode as specified by the configuration information 412-1, the device manager 440-1 need not register with the management resource 450 and thus enables use of UNLOCKED functionality 430-1 such as functionality F1, functionality F2, functionality F3, and functionality F4.

Note that even though certain functionality such as functionality F3 and functionally F4 may unlocked for use, such functionality F3 and F4 may require that the medical device 110-1 be able to communicate (over any suitable communication link) with management resource 450 (such as one or more remote servers) in order to support such functionality. In one embodiment, the management resource 450 is configured to provide any suitable data that is required to support functionality F3 and at F4. In a reverse direction, because the medical device 110-1 is UNLOCKED, the medical device 410-1 can be configured to provide any suitable data over network GHI to the management resource 450 to support functionality F3 and F4.

In furtherance of retrieving data from or transmitting data to the management resource, the medical device 110-1 includes network access information 420-1 indicating how to connect to the respective management resource 450. Using the network access information 420-1, the device manager 440-1 of the medical device 410-1 establishes a respective connection with network GHI to communicate with management resource 450. Each of the medical devices 410 in the network environment 400 can be configured to operate in a similar manner.

Figure 5:
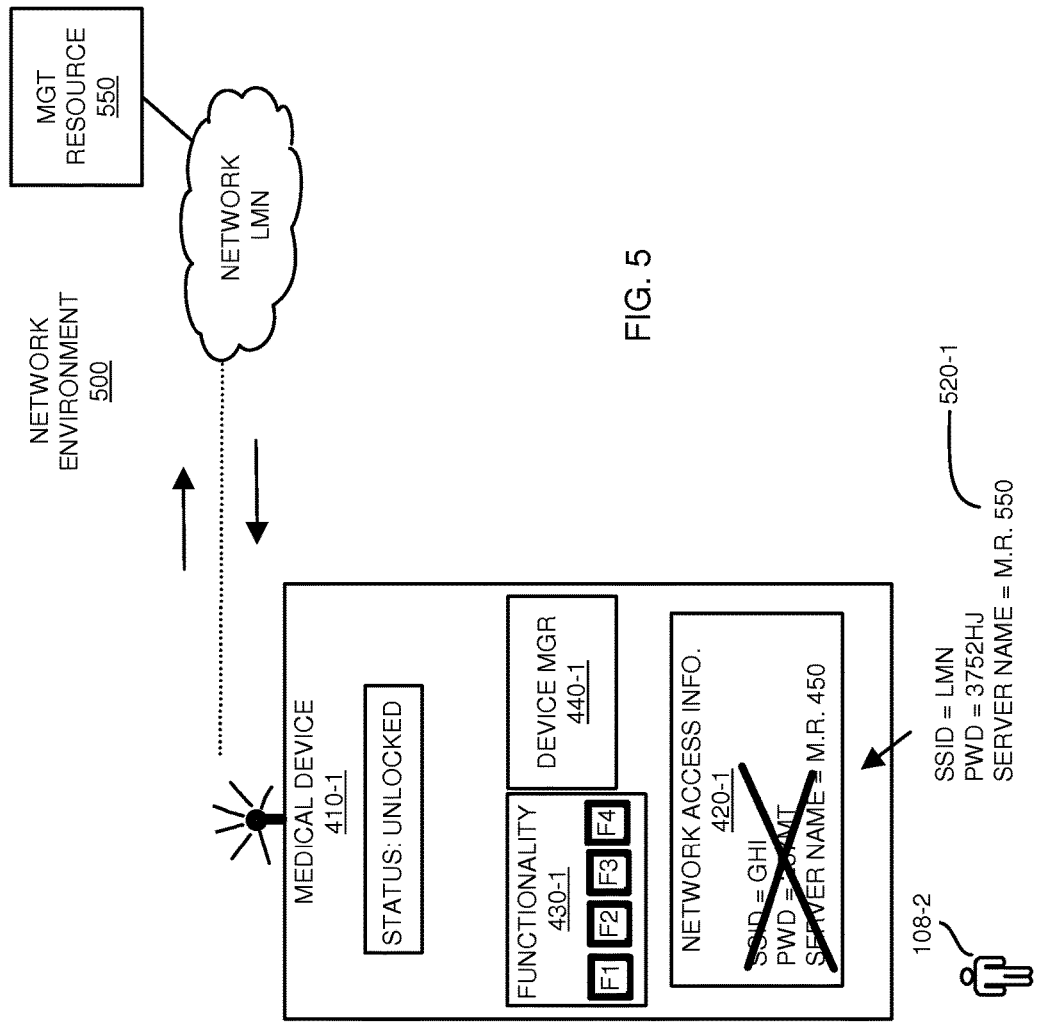
FIG. 5 is an example diagram illustrating modification of network access information in a medical device and subsequent use of the medical device in an unlocked operational mode according to embodiments herein.

FIG. 5 is an example diagram illustrating modification of network access information in a medical device and subsequent use of the medical device in an unlocked operational mode according to embodiments herein.

In this example embodiment, assume that the medical device 410-1 is removed from network environment 400 previously discussed in FIG. 4 and is instead operated in network environment 500 shown in FIG. 5. In such an instance, because the medical device 410-1 is no longer within the wireless communication range of the network environment 400, the device manager 440-1 may not be able to use network access information 420-1 to communicate with the management resource 450.

However, user 408-2 can overwrite the network access information 420-1 with new network access information 520-1. In this example, the updated network access information 520-1 overwriting network access information 420-1 indicate a corresponding network LMN and password 3752HJ in which to communicate with the target management resource 550. Upon activation of medical device 410-1, because the configuration setting information 412-1 indicates that the medical device 410-1 is set to an UNLOCKED mode, the device manager 440-1 enables all functionality 430-1 including functionality F1, functionality F2, functionality F3, and functionality F4. This functionality requires connectivity with respect to a network, the device manager 440-1 utilizes the replacement network access information 520-1 to communicate with management resource 550 associated with network LMN.

As previously discussed, the device manager 440-1 may be required to establish the respective communication link over network LMN to management resource 550 in order to transmit and/or receive data with respect to executing functionality F3 and F4. In other words, functionality F3 and F4 may require connection with a corresponding management resource 550.

Thus, in this example embodiment, because each of the medical devices 410 is set to a respective UNLOCKED mode, the respective medical devices can be reconfigured for use in any network that supports functionality F3 and F4. This illustrates how the respective medical devices 410 can be misappropriated such as stolen or inadvertently removed from one network and used in another network because they are not LOCKED.

Figure 9:
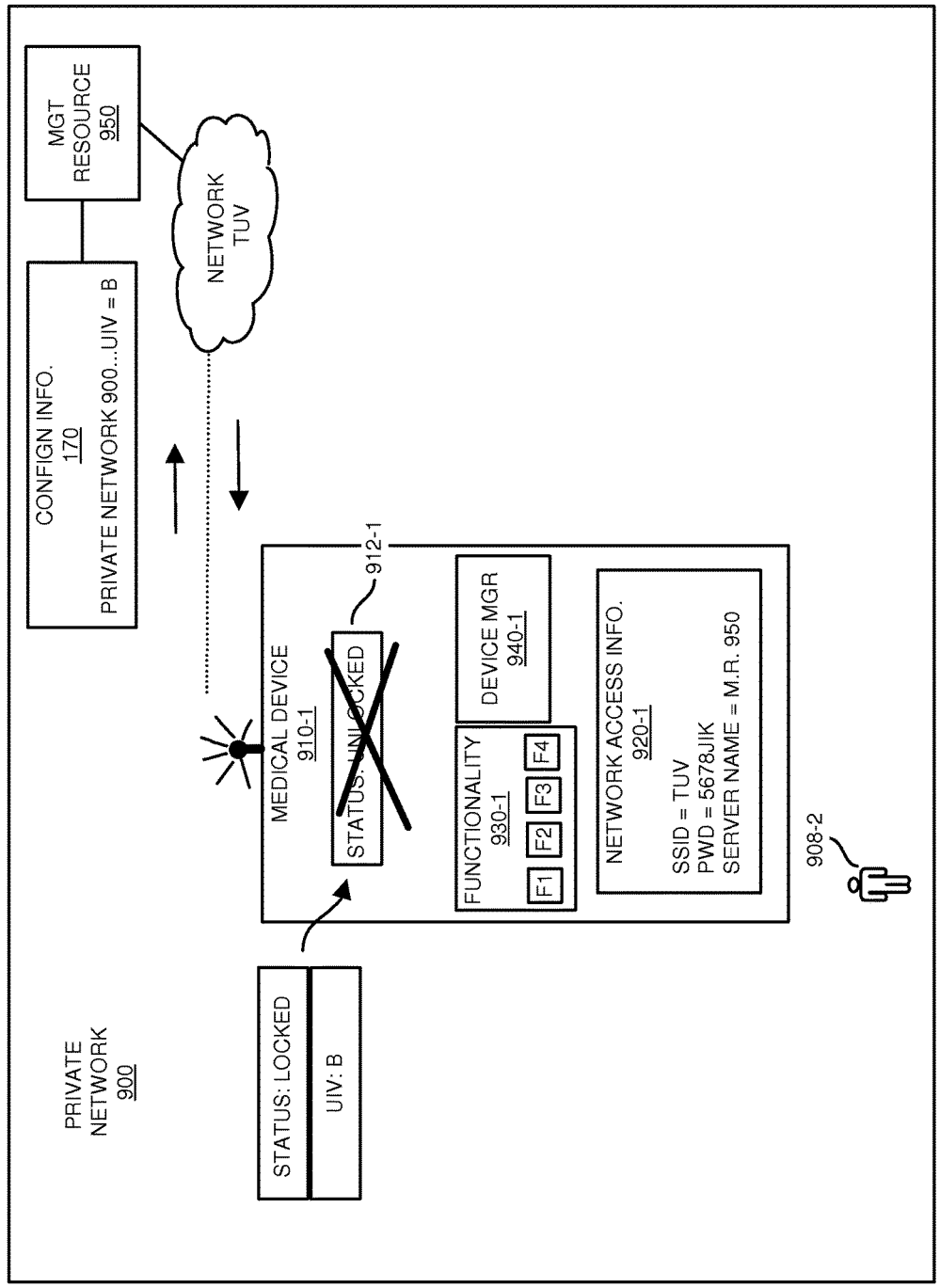
FIG. 9 is an example diagram illustrating modifying configuration of a medical device from being set to an unlocked mode to a locked mode according to embodiments herein.

FIG. 9 is an example diagram illustrating modification of configuration information in a medical device to switch from an UNLOCKED mode to a LOCKED mode according to embodiments herein.

Embodiments herein can further include binding a respective UNLOCKED medical device to a respective private network. More specifically, assume that the medical device 910-1 is initially set to the UNLOCKED mode as shown and as previously discussed. The user 908-2 operates medical device 910-1. This prompts the device manager 940-1 of the medical device 110-1 to utilize network access information 920-1 to establish a respective communication link and communicate through network TUV with management resource 950.

Via configuration information 912-1, the device manager 940-1 detects that the medical device 110-1 is initially set to an UNLOCKED mode. To bind the medical device 910-1 to the private network 900, the management resource 950 communicates a LOCK command and unique identifier value B (such as a key value assigned to private network 900) over network TUV to the device manager 940-1 in medical device 910-1. In response to receiving the LOCK command, the device manager 940-1 initiates modification of configuration information 912-1 to indicate that the medical device 910-1 has been changed to a LOCKED mode. Additionally, the device manager 940-1 modifies the configuration information 912-1 to include the unique identifier value B. Subsequent to updating the configuration information 912-1, the medical device 910-1 must be used and obtain authorization from the management resource 950 in private network 900 in order to execute functionality F3 and F4.

Locking the medical device 110-1 and providing the unique identifier value B assigned to the private network 900 binds the medical device 110-1 to the private network 900. Thereafter, after binding, the medical device 910-1 must be operated in the private network 900 and verified/authorized by the management resource 950 in a manner as previously discussed in order for the device manager 940-1 to enable functionality F3 and F4. In a similar manner as previously discussed, the device manager 940-1 can be configured to enable functionality F1 and F2 as a default when the medical device 910-1 is used outside of the private network 900.

Figure 6:
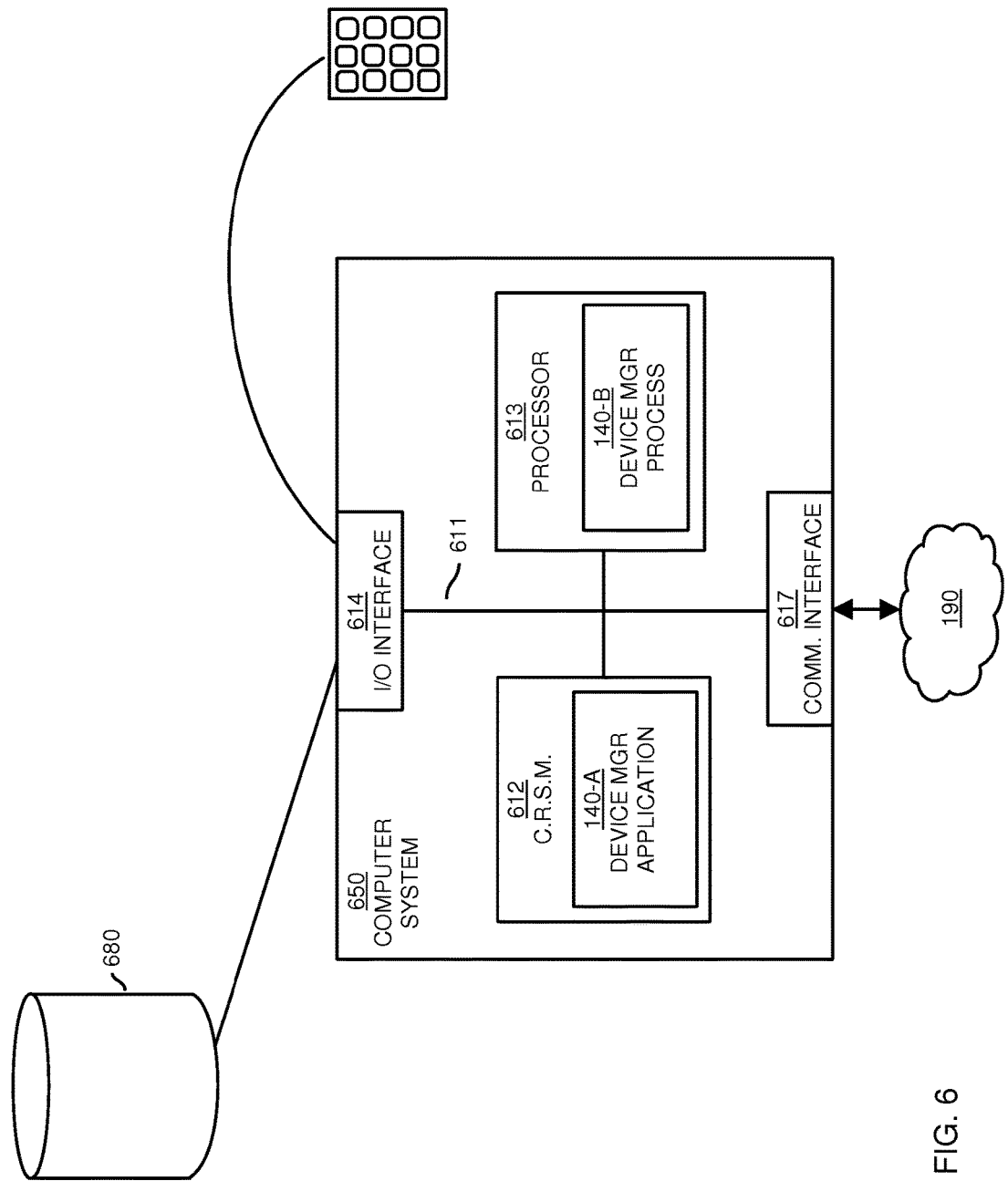
FIG. 6 is a diagram illustrating an example computer architecture in which to execute any of the functionality according to embodiments herein.

FIG. 6 is an example block diagram of a computer device for implementing any of the operations as discussed herein.

As shown, computer system 650 such as a computer device of the present example in any medical device such as medical device 110-1, medical device 110-2, medical device 410-1, 910-1, etc., can include an interconnect 611 that couples computer readable storage media 612 such as a non-transitory type of media (i.e., any type of hardware storage medium, tangible storage medium, etc.) in which digital information can be stored and retrieved, a processor 613 (e.g., one or more processor devices or hardware processors), I/O interface 614, and a communications interface 617. Communications interface 617 enables the computer system 650 to communicate with other network elements present in a corresponding network environment.

I/O interface 614 provides connectivity to a repository 680 and, if present, other devices such as a playback device, display screen, keypad, a computer mouse, etc.

Computer readable storage medium 612 can be any hardware storage resource or device such as memory, optical storage, hard drive, floppy disk, etc. In one embodiment, the computer readable storage medium 612 stores instructions and/or data.

Communications interface 617 enables the computer system 650 and corresponding processor 613 to communicate with network elements in communication environment 100 retrieve information from remote sources such as network elements and communicate with other computers. I/O interface 614 enables processor 613 to retrieve stored information from repository 680.

As shown, computer readable storage media 612 is encoded with device manager application 140-A (e.g., software, firmware, computer code, etc., associated with device manager 140) executed by processor 613. Device manager application 140-A can be configured to include instructions to implement any of the operations as discussed herein.

During operation of one embodiment, processor 613 accesses computer readable storage media 612 via the use of interconnect 611 in order to launch, run, execute, interpret or otherwise perform the instructions in device manager application 140-A stored on computer readable storage medium 612.

Execution of the device manager application 140-A produces processing functionality such as device manager process 140-B in processor 613. In other words, the device manager process 140-B associated with processor 613 represents one or more aspects of executing device manager application 140-A within or upon the processor 613 in the computer system 650.

Those skilled in the art will understand that the computer system 650 can include other processes and/or software and hardware components, such as an operating system that controls allocation and use of hardware resources to execute device manager application 140-A.

In accordance with different embodiments, note that computer system 650 may be any of various types of devices, including, but not limited to, a mobile computer, a medical device, infusion pump, a personal computer system, a server resource, a wireless device, base station, phone device, desktop computer, laptop, notebook, netbook computer, mainframe computer system, handheld computer, workstation, network computer, application server, storage device, a consumer electronics device such as a camera, camcorder, set top box, mobile device, video game console, handheld video game device, a peripheral device such as a switch, modem, router, or in general any type of computing or electronic device. The computer system 750 may reside at any location or can be included in any suitable resource in communication environment 100 to implement functionality as discussed herein.

Functionality supported by the different resources will now be discussed via flowcharts in FIGS. 7-8. Note that the steps in the flowcharts below can be executed in any suitable order.

Figure 7:
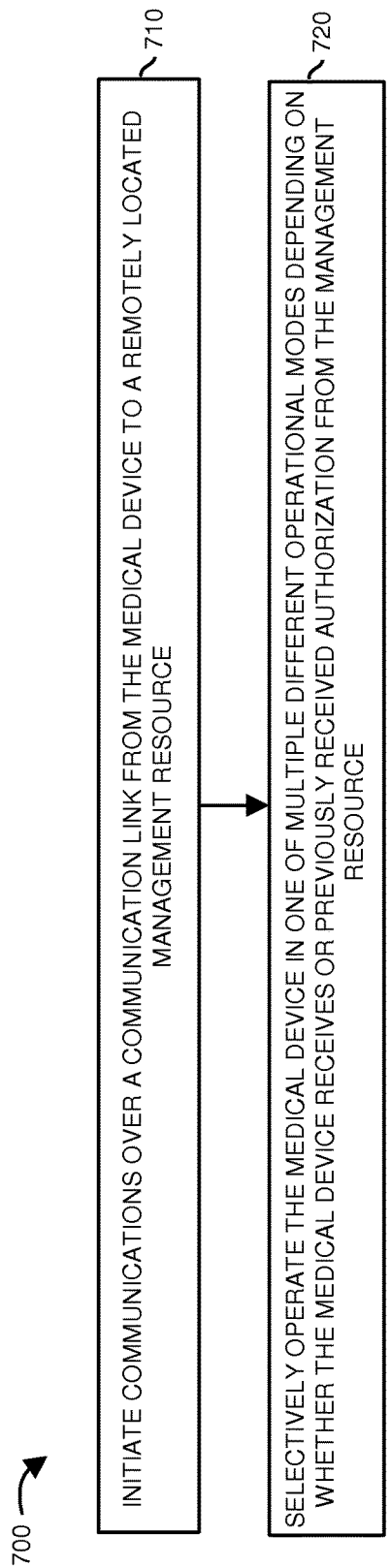
FIG. 7 is an example diagram illustrating a method according to embodiments herein.

FIG. 7 is a flowchart 700 illustrating an example method according to embodiments herein. Note that there will be some overlap with respect to concepts as discussed above.

In processing block 710, the device manager 140-1 in medical device 110-1 initiates communications over a communication link 127-1 from the medical device 110-1 to a remotely located management resource 150.

In processing block 720, the device manager 140-1 selectively operates the medical device 110-1 in one of multiple different operational modes (such as enables any of one or more different functions) depending on whether the device manager 140-1 of medical device 110-1 currently receives or previously received authorization/verification from the management resource 150.

Figure 8:
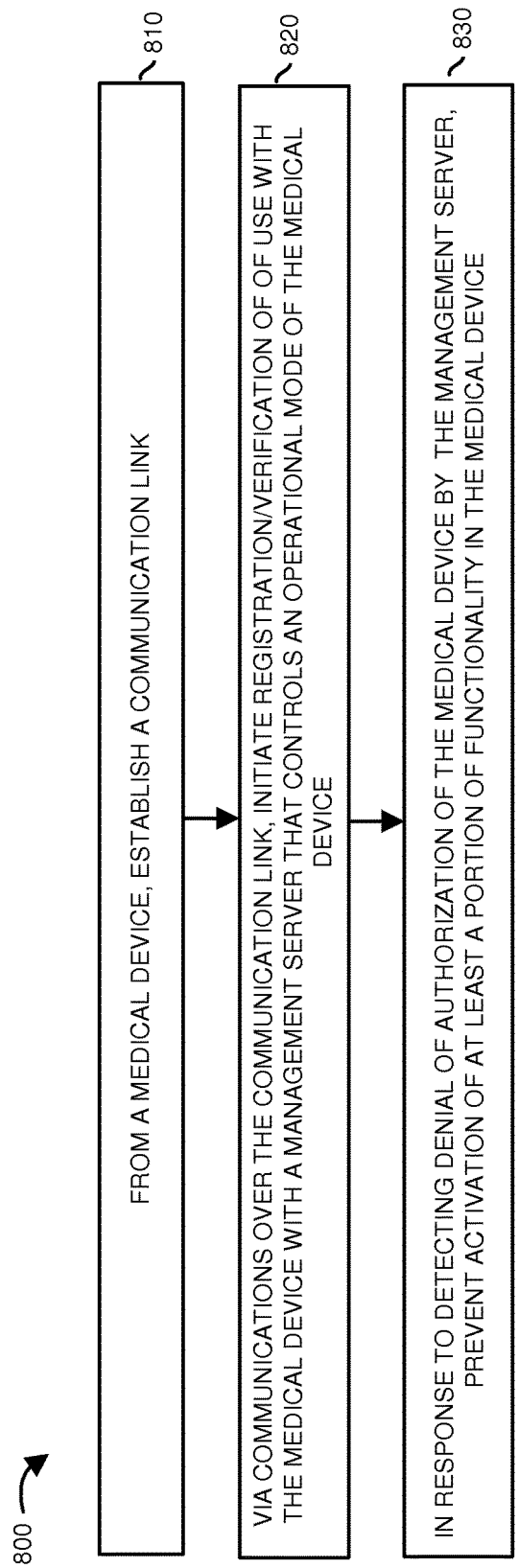
FIG. 8 is an example diagram illustrating a method according to embodiments herein.

FIG. 8 is a flowchart 800 illustrating an example method according to embodiments. Note that there will be some overlap with respect to concepts as discussed above.

In processing block 810, the device manager 140-1 of the medical device 110-1 establishes a communication link 127-1 between medical device 110-1 and the wireless access point in network XYZ.

In processing block 820, via communications over the communication link 127-1, the device manager 140-1 initiates registration/verification of use of the medical device 110-1 with management resource 150. As previously discussed, the device manager 140-1 controls an operational mode of the medical device 110-1 based on feedback from the management resource 150. Controlling an operational mode of the medical device 110-1 includes enabling all or a less-than-all portion of functionality 130-1.

In processing block 830, in response to detecting an inability of the medical device 110-1 to register/verify the use with the management server 150, the device manager 140-1 prevents activation of at least a portion of functionality supported by the medical device 110-1. For example, as previously discussed, the device manager 140-1 can prevent use of functions F3 and F4, but allow use of functions F1 and F2 in response to detecting a condition such as that the medical device 110-1 has been currently or previously denied authentication from a management server 150 or other server resource that performs authorization checks.

In certain instances, if desired, the device manager 140-1 can be configured to prevent use of all of functionality 130-1 in response to a denial of authentication from a resource such as the management server 150.

Note again that techniques herein are well suited for inhibiting theft of medical devices. However, it should be noted that embodiments herein are not limited to use in such applications and that the techniques discussed herein are well suited for other applications as well.

Based on the description set forth herein, numerous specific details have been set forth to provide a thorough understanding of claimed subject matter. However, it will be understood by those skilled in the art that claimed subject matter may be practiced without these specific details. In other instances, methods, apparatuses, systems, etc., that would be known by one of ordinary skill have not been described in detail so as not to obscure claimed subject matter. Some portions of the detailed description have been presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm as described herein, and generally, is considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has been convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining" or the like refer to actions or processes of a computing platform, such as a computer or a similar electronic computing device, that manipulates or transforms data represented as physical electronic or magnetic quantities within memories, registers, or other information storage devices, transmission devices, or display devices of the computing platform.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting. Rather, any limitations to the invention are presented in the following claims.

We claim:

1. A method comprising:
in a medical device:
  accessing configuration information assigned to the medical device;
  initiating communications over a communication link from the medical device to a remotely located management resource over a network to register the medical device for use in a private medical network environment to which the medical device is assigned for use, the communications initiated over the communication link in response to detecting that the configuration information indicates that the medical device is assigned a lock mode in which the medical device requires confirmation by the remotely located management resource to execute a first modal operation of the medical device;
  receiving authorization from the remotely located management resource, the authorization indicating that the medical device has been verified for execution of the first modal operation in the private medical network environment;
  providing continued first modal operation of the medical device while the medical device moves outside of a wireless communication range of the private medical network environment; and
  switching from the first modal operation to second modal operation of the medical device in response to detecting subsequent denial of authorization of further use of the medical device, the denial of authorization occurring in response to an attempt to authorize use of the first modal operation of the medical device in a foreign environment outside the wireless communication range of the private medical network environment.

2. The method as in claim 1, wherein the medical device is a medical infusion pump supporting first functionality and second functionality, the method further comprising:
in response to receiving the authorization from the remotely located management resource: enabling both the first functionality and the second functionality in the medical infusion pump:
in response to detecting the denial of authorization:
enabling the medical infusion pump to execute the first functionality, and
preventing the medical infusion pump from executing the second functionality.

3. The method as in claim 1, wherein the medical device is a medical infusion pump configured to support first functionality and second functionality, the method further comprising:
in response to being denied authorization from the management resource: i) enabling the medical infusion pump to execute the first functionality, and ii) preventing execution of the second functionality in the medical infusion pump, and iii) causing a notification to be presented to a user of the medical device.

4. The method as in claim 3, wherein the first functionality supports pumping fluid from the medical infusion pump to a recipient; and
wherein the second functionality supports retrieval of drug information over a network connection from a remote server resource disparately located with respect to the medical infusion pump.

5. The method as in claim 1, wherein switching to the second operational mode includes disabling a less-than-all portion of functionality supported by the first modal operation.

6. The method as in claim 1, wherein the communication link is a wireless communication link to a wireless access point in the private medical network environment, the method further comprising:
establishing the wireless communication link in response to detecting activation of the medical device to perform an operation.

7. The method as in claim 1, wherein the management resource resides in a private network of a medical service provider, the management resource accessible by the medical device during conditions in which the medical device resides within a wireless communication range of the private medical network environment.

8. The method as in claim 1 further comprising:
in response to detecting the subsequent denial of authorization at the medical device, providing notification to an operator of the medical device, the notification indicating a medical service provider to which the medical device belongs.

9. The method as in claim 1 further comprising:
in response to detecting the subsequent denial of authorization at the medical device, producing a notification to indicate that at least a portion of functionality of the medical device is disabled based on an inability of the medical device to commuicate with the management resource.

10. The method as in claim 1 further comprising:
obtaining a unique identifier value assigned to the medical device; and
communicating the unique identifier value over the communication link to the remotely located management resource to obtain the authorization.

11. The method as in claim 10, wherein the unique identifier value is assigned to a healthcare enterprise to which the medical device belongs, the healthcare enterprise assigned use of the medical device in the private medical network environment.

12. The method as in claim 1, wherein establishing the communication link further comprises:
obtaining network information specifying a name of a wireless access point in the private medical network environment, the network information including a password to obtain access to the remotely located management resource through the wireless access point; and
utilizing the name of the wireless access point and the password to establish the communication link through the wireless access point to communicate with the remotely located management resource.

13. The method as in claim 12 further comprising:
obtaining a unique identifier value assigned to the medical device;
forwarding the unique identifier value over the communication link to the remotely located management resource; and
receiving a response from the remotely located management resource verifying the medical device, the response indicating that the medical device is authorized to operate with full functionality.

14. The method as in claim 1 further comprising:
at the medical device, receiving subsequent authorization from the remotely located management resource via communications over the private medical network environment; and
switching from the second modal operation to the first modal operation of the medical device in response to receiving the subsequent authorization from the remotely located management resource.

15. The method as in claim 1, wherein the second modal operation of the medical device supports at least one but less than all of multiple fluid pump operations supported by the first modal operation of the medical device.

16. The method as in claim 1, wherein the first modal operation of the medical device supports a first set of fluid pump operations; and
wherein the second modal operation of the medical device supports a second set of fluid pump operations, the second set of the fluid pump operations being different than the first set of fluid pump operations.

17. The method as in claim 1, wherein both the first modal operation and the second modal operation of the medical device support delivery of a fluid from the medical device to a recipient; and
wherein the medical device is programmed with communication settings to communicate through the private medical network environment with the remotely located management resource to obtain the authorization.

18. A computer system comprising:
computer processor hardware in a medical device; and
a hardware storage resource coupled to the computer processor hardware, the hardware storage resource storing instructions that, when executed by the computer processor hardware, causes the computer processor hardware to perform operations of:
accessing configuration information assigned to the medical device;

initiating communications over a communication link from the medical device to a remotely located management resource over a network to register the medical device for use in a private medical network environment to which the medical device is assigned for use, the communications initiated over the communication link in response to detecting that the configuration information indicates that the medical device is assigned a lock mode in which the medical device requires confirmation by the remotely located management resource to execute a first modal operation of the medical device;

receiving authorization from the remotely located management resource, the authorization indicating that the medical device has been verified for execution of the first modal operation in the private medical network environment;

providing continued first modal operation of the medical device while the medical device moves outside of a wireless communication range of the private medical network environment; and switching from the first modal operation to second modal operation of the medical device in response to detecting subsequent denial of authorization of further use of the medical device, the denial of authorization occurring in response to an attempt to authorize use of the first modal operation of the medical device in a foreign environment outside the wireless communication range of the private medical network environment.

19. The computer system as in claim 18, wherein the medical device is a medical infusion pump configured to support first functionality and second functionality, the computer processor hardware further performing operations of:
at a first instance in time, in response to receiving authorization from the management resource, executing the medical device in the first operational mode including: enabling both the first functionality and the second functionality in the medical infusion pump.

20. The computer system as in claim 19, wherein the computer processor hardware further performs operations of:
at a second instance in time, subsequent to the first instance in time, in response to denial of the subsequent authorization of use of the medical device while the medical device is outside the private medical network environment, executing the medical device in the second operational mode including: i) enabling the medical infusion pump to execute the first functionality, and ii) preventing execution of the second functionality in the medical infusion pump.

21. The computer system as in claim 20, wherein the first functionality supports pumping fluid from the medical infusion pump to a recipient; and
wherein the second functionality supports retrieval of drug information over a network connection from a remote server resource disparately located with respect to the medical infusion pump.

22. The computer system as in claim 18, wherein the computer processor hardware further performs operations of:
establishing the wireless communication link with the wireless access point in response to detecting activation of the medical device.

23. The computer system as in claim 18, wherein the remotely located management resource resides in a private network of a medical service provider, the remotely located management resource accessible by the medical device during conditions in which the medical device resides within wireless communication range of the wireless access point, which resides in the private medical network environment, the computer processor hardware further performing operations of:
limiting operation of the medical device in response to being denied authorization through the wireless access point.

24. The computer system as in claim 18, wherein the computer processor hardware further performs operations of:
in response to detecting the denial of subsequent authorization of use of the medical device, providing notification to an operator of the medical device, the notification indicating a medical service provider to which the medical device belongs.

25. The computer system as in claim 18, wherein the computer processor hardware further performs operations of:
in response to detecting the denial of subsequent authorization of use of the medical device, producing a notification to indicate that at least a portion of functionality of the medical device is disabled based on the denial.

26. The computer system as in claim 18, wherein the computer processor hardware further performs operations of:
obtaining a unique identifier value assigned to the medical device; and
communicating the unique identifier value over the communication link through the wireless access point to the remotely located management resource to verify use of the medical device in the private medical network environment.

27. Computer-readable hardware storage having instructions stored thereon, the instructions, when carried out by computer processor hardware in a medical device, causes the computer processor hardware to perform operations of:
accessing configuration information assigned to the medical device;
initiating communications over a communication link from the medical device to a remotely located management resource over a network to register the medical device for use in a private medical network environment to which the medical device is assigned for use, the communications initiated over the communication link in response to detecting that the configuration information indicates that the medical device is assigned a lock mode in which the medical device requires confirmation by the remotely located management resource to execute a first modal operation of the medical device;
receiving authorization from the remotely located management resource, the authorization indicating that the medical device has been verified for execution of the first modal operation in the private medical network environment;
providing continued first modal operation of the medical device while the medical device moves outside of a wireless communication range of the private medical network environment; and
switching from the first modal operation to second modal operation of the medical device in response to detecting subsequent denial of authorization of further use of the medical device, the denial of authorization occurring in response to an attempt to authorize use of the first modal operation of the medical device in a foreign environment outside the wireless communication range of the private medical network environment.

* * * * *